United States Patent [19]

Okada et al.

[11] Patent Number: 4,968,505

[45] Date of Patent: Nov. 6, 1990

[54] LONG-ACTING DICLOFENAC SODIUM PREPARATION

[75] Inventors: Minoru Okada, Kioroshihigashi; Syuichi Kasai, Narita; Akira Iwasa, Yotsukaido, all of Japan

[73] Assignee: SS Pharmaceutical Company, Ltd., Tokyo, Japan

[21] Appl. No.: 353,016

[22] Filed: May 17, 1989

[30] Foreign Application Priority Data

Aug. 16, 1988 [JP] Japan .................................. 63-203498

[51] Int. Cl.⁵ .............................................. A61K 9/00
[52] U.S. Cl. .................................... 424/400; 424/458; 424/461; 424/462; 424/493; 424/494; 424/495; 424/497; 424/498
[58] Field of Search ............... 424/458, 498, 495, 400, 424/493, 494, 97, 461, 462; 427/3

[56] References Cited

U.S. PATENT DOCUMENTS

4,726,951  2/1988  Panoz et al. ......................... 424/498
4,814,183  3/1989  Zentner ................................ 924/443

Primary Examiner—Thurman K. Page
Attorney, Agent, or Firm—Oblon, Spivak, McClelland, Maier & Neustadt

[57] ABSTRACT

A long-acting diclofenac sodium preparation is disclosed. The preparation comprises a sustained-release diclofenac sodium component which is prepared by coating a sustained-release coat onto a pharmaceutical composition comprising diclofenac sodium and an organic acid. It can decrease the maximum blood concentration of diclofenac by suppressing and controlling the rate of release of diclofenac sodium and maintain the blood concentration of diclofenac constant for a considerably long period of time. The risk of side-effect occurrences is reduced and patients is released from frequent administration of the medicine.

14 Claims, 4 Drawing Sheets

LONG-ACTING DICLOFENAC SODIUM PREPARATION

BACKGROUND OF THE INVENTION

1. Field of the Invention:

The present invention relates to a long-acting diclofenac sodium preparation, and, more particularly, to a long-acting diclofenac sodium preparation comprising a sustained-release diclofenac sodium component which is prepared by coating a sustained-release coat onto a pharmaceutical composition comprising diclofenac sodium and an organic acid.

2. Description of the Background:

The utility of diclofenac sodium, which is a kind of non-steroidal anti-inflammatory drug, is highly appreciated because of its strong anti-inflammatory and analgesic actions. Diclofenac sodium is thus widely used clinically. The blood concentration half life of this compound is, however, very short. This necessitates nuisance of administering the compound three times a day, each time after meal. This nuisance leads to patient non-compliance such as failure of taking the compound. This is the situation unfavorable to the proper clinical control. Another problem involving diclofenac sodium administration is a significant side effect due to a rapid increase in the blood concentration. Demand has therefore existed for the development of a long-acting diclofenac sodium preparation which is capable of exhibiting the effect of diclofenac sodium in a most safe and efficacious manner over a long period of time.

In view of this situation, the present inventors carried out research related to a sustained-release diclofenac sodium component. As a result, the inventors have found that a sustained-release diclofenac sodium component which is prepared by coating a sustained-release coat onto a pharmaceutical composition comprising diclofenac sodium and an organic acid is able to suppress the diclofenac concentration in blood and to maintain the concentration constant over a prolonged period of time.

SUMMARY OF THE INVENTION

Accordingly, an object of the present invention is to provide a long-acting diclofenac sodium preparation comprising a sustained-release diclofenac sodium component which is prepared by coating a sustained-release coat onto a pharmaceutical composition comprising diclofenac sodium and an organic acid.

Other objects, features and advantages of the invention will hereinafter become more readily apparent from the following description.

DETAILED DESCRIPTION OF THE INVENTION AND PREFERRED EMBODIMENTS

In this invention, the pharmaceutical composition comprising diclofenac sodium and an organic acid contains at least 2 parts by weight, especially preferably 2-50 parts by weight, of organic acid per 100 parts by weight of diclofenac sodium. Given as examples of organic acids which can be used are citric acid, ascorbic acid, fumaric acid, tartaric acid, succinic acid, malic acid, and adipic acid, as well as mixtures of two or more of these acids.

An organic acid and diclofenac sodium may be mixed or each of them may compose separate layers. Formulating an organic acid and diclofenac sodium in separate layers can be achieved, for example, by applying a layer of fine powders of organic acid onto tablets, granules, fine granules, beads, or the like containing diclofenac sodium and by compress-molding the same. Alternatively, fine powders of organic acid may be adhered onto the surfaces of diclofenac sodium tablets, granules, fine granules, beads, or the like.

Any compounds conventionally used as a sustained-release coat can be used for the purpose of this invention. Specific examples which can be given include water insoluble polymers such as ethylcellulose, aminoalkyl methacrylate copolymer polyvinyl acetate, polyvinyl chloride, polyethylene, and the like; intestinally soluble polymers such as cellulose acetate phthalate, hydroxypropyl methylcellulose phtharate, hydroxypropyl methylcellulose acetate succinate, carboxymethylethylcellulose, styrene acrylic acid copolymer, methacrylic acid copolymer, maleic anhydrous acid copolymer, shellac, and the like; paraffin waxes such as paraffin, microcrystalline wax, and the like; higher alcohols such as stearyl alcohol, cetyl alcohol, and the like; higher fatty acid esters such as glycerine fatty acid esters, hydrogenated oils, carnauba wax, beeswax, Japan (haze) wax, and the like; and higher fatty acids such as stearic acid, palmitic acid, myristic acid, behenic acid, and the like (or the sodium, calcium or magnesium salts of these higher fatty acids). Among these, preferable compounds are water insoluble polymers and intestinally soluble polymers which are soluble in water at an acidity level in the range of about pH 5.5-7, especially of about 7.

The above compounds may be used as a sustained-release coat either individually or in combination. Other compounds may also be formulated into sustained-release coats. Given as examples of ideal sustained-release coats are an intestinally soluble coat comprising 1 part by weight of methacrylic acid copolymer S (methacrylic acid-methyl methacrylate copolymer containing 25.0-34.5% of methacrylic acid on dry basis; trade name: Eudragit S), 0.03-0.3 part by weight of glycerine fatty acid ester, and 0.01-1.5 parts by weight of talc, and a water insoluble coat comprising 1 part by weight of water insoluble polymer, 0.2-0.5 part by weight of polyvinyl pyrrolidone, and 0.01-1.5 parts by weight of talc.

In the preparation of sustained-release diclofenac sodium component of this invention, a pharmaceutical composition containing diclofenac sodium and an organic acid, and, optionally, a suitable additives is microencapsulated by a conventional method. Alternatively, this pharmaceutical composition as is, or after the addition of suitable additives such as binders, lubricants, disintegrators, vehicles, disintegration retarding agents, plasticizers, coloring agents, flavors, and the like, is formed into tablets, granules, fine granules, beads, or the like according to conventional methods. Then, a sustained-release coat is applied onto them.

The amount of the sustained-release coat to be used varies depending on the types of preparation. Usually, an amount ranging from 1 to 80% by weight based on the amount of the pharmaceutical composition is applicable. In the case of intestinally soluble coats, an amount of 10–80% by weight, especially of 10–60% by weight, is preferable. An amount of 1–80% by weight, especially of 3–60% by weight, is preferable for water insoluble coats.

A sustained-release diclofenac sodium component thus prepared may be used as is as a long-acting diclofenac sodium preparation. In another embodiment, this sustained-release diclofenac sodium component preparation is combined with diclofenac sodium component to which no sustained-release treatment is applied to produce a long-acting diclofenac sodium preparation.

The latter preparation to which sustained-release diclofenac sodium component and rapid-release diclofenac sodium component are formulated may be prepared by mixing the both or by forming layers of each diclofenac sodium component. The proportion of sustained-release diclofenac sodium component and rapid-release diclofenac sodium component& in the preparation varies depending on the intended diclofenac concentration in blood and the desired lasting time duration. Usually, a preferable amount of diclofenac sodium in the rapid-release diclofenac sodium component in total amount of diclofenac sodium in the preparation is 10–50% by weight, with especially preferable range being 20–40% by weight.

There are no specific limitations as to the types of long-acting diclofenac sodium preparation of this invention. It may be powders, fine granules, granules, beads, capsules, tablets, or the like.

The long-acting diclofenac sodium preparation of this invention prepared as fully described above can decrease the maximum blood concentration of diclofenac by suppressing and controlling the rate of release of diclofenac sodium from the preparation. It can maintain the blood concentration of diclofenac constant for a considerably long period of time. This reduces the risk of side-effect occurrences and, at the same time, can provide a prescription of a once-a-day-administration type.

Other features of the invention will become apparent in the course of the following description of the exemplary embodiments which are given for illustration of the invention and are not intended to be limiting thereof.

EXAMPLES

Example 1

(1) Preparation of non-coated granules A:

800 g of diclofenac sodium, 200 g of citric acid, and 200 g of corn starch were mixed and pulverized. The fine powders thus prepared were processed to produce spherical granules, using 600 g of purified sucrose that was obtained by shifting through 20–28 mesh as a core, while spraying a solution of 25 g of hydroxypropyl cellulose in 475 g of ethyl alcohol. The granules were then dried for 3 hours at 55° C. These dried granules were then passed through a 14 mesh followed by passage through a 28 mesh. The granules which did not go through the 28 mesh were taken as non-coated granules A. The formulation of this non-coated granules A was as follows:

| Component | % by weight |
| --- | --- |
| Diclofenac sodium | 43.7 |
| Citric acid | 11.0 |
| Corn starch | 11.0 |
| Purified sucrose | 32.9 |
| Hydroxypropyl cellulose | 1.4 |
| Total | 100.0 |

(2) Preparation of long-acting granules A-1 of this invention 600 g of non-coated granules A was placed into a coating apparatus with a fluidized bed. The granules were spray coated with 1,263 g of a coating liquid having the following composition according to a conventional method to produce long-acting granules A-1. The weight of the coat was about 8% of the weight of the non-coated granules.

| Component | % by weight |
| --- | --- |
| Ethylcellulose | 2.7 |
| Polyvinyl pyrrolidone K30 | 0.9 |
| Talc | 0.2 |
| Ethyl alcohol | 96.2 |
| Total | 100.0 |

Example 2

Preparation of long-acting granules A-2 of this invention having an exterior rapid-releasing layer 50.7 g of diclofenac sodium and 149.3 g of corn starch were mixer and pulverized. The fine powders thus produced were processed to produce spherical granules, using 500 g of the long-acting granules A-1 as a core, while spraying a solution of 4 g of hydroxypropyl cellulose in 76 g of ethyl alcohol. The granules were then dried for 2 hours at 55° C. to produce long-acting granules A-2 of this invention having an exterior rapid-releasing layer.

Example 3

(1) Preparation of non-coated granules B:

1,000 g of diclofenac sodium, 30 g of fumaric acid, and 170 g of corn starch were mixed and pulverized. The fine powders thus produced were processed to produce spherical granules, using 600 g of purified sucrose that was obtained by shifting through 20–28 mesh as a core, while spraying a solution of 25 g of hydroxypropyl cellulose in 475 g of ethyl alcohol. The granules were then dried for 3 hours at 55° C. These dried granules were then passed through a 14 mesh followed by passage through a 28 mesh. The granules which did not go through the 28 mesh were taken as non-coated granules B. The formulation of this non-coated granules B was as follows:

| Component | % by weight |
| --- | --- |
| Diclofenac sodium | 54.8 |
| Fumaric acid | 1.6 |
| Corn starch | 9.3 |
| Purified sucrose | 32.9 |
| Hydroxypropyl cellulose | 1.4 |

| Component | % by weight |
|---|---|
| Total | 100.0 |

(2) Preparation of long-acting granules B-1 of this invention 600 g of non-coated granules B was placed into a coating apparatus with fluidized bed. The granules were spray coated with 1,667 g of a coating liquid having the following composition according to a conventional method to produce long-acting granules B-1.

The amount of the coat was about 20% based on the weight of the non-coated granules.

| Component | % by weight |
|---|---|
| Methacrylic acid copolymer S | 6.5 |
| Glycerine fatty acid ester | 0.5 |
| Talc | 0.2 |
| Ethyl alcohol | 92.8 |
| Total | 100.0 |

Example 4

(1) Preparation of non-coated granules C:

800 of diclofenac sodium, 200 g of fumaric acid, and 200 g of corn starch were mixed and pulverized. The fine powders thus produced were processed to produce spherical granules, using 600 g of purified sucrose that was obtained by shifting through 20–28 mesh as a core, while spraying a solution of 25 g of hydroxypropyl cellulose in 475 g of ethyl alcohol. The granules were then dried for 3 hours at 55° C. These dried granules were then passed through a 14 mesh followed by passage through a 28 mesh. The granules which did not go through the 28 mesh were taken as non-coated granules C. The formulation of this non-coated granules C was as follows:

| Component | % by weight |
|---|---|
| Diclofenac sodium | 43.7 |
| Fumaric acid | 11.0 |
| Corn starch | 11.0 |
| Purified sucrose | 32.9 |
| Hydroxypropyl cellulose | 1.4 |
| Total | 100.0 |

(2) Preparation of long-acting granules C-1 of this invention 600 g of non-coated granules C was placed into a coating apparatus with fluidized bed. The granules were spray coated with 1,667 g of a coating liquid having the following composition according to a conventional method to produce long-acting granules C-1. The amount of the coat was about 20% based on the weight of the non-coated granules.

| Component | % by weight |
|---|---|
| Methacrylic acid copolymer S | 6.5 |
| Glycerine fatty acid ester | 0.5 |
| Talc | 0.2 |
| Ethyl alcohol | 92.8 |
| Total | 100.0 |

Example 5

(1) Preparation of non-coated granules D:

700 g of diclofenac sodium, 350 g of fumaric acid, and 150 g of corn starch were mixed and pulverized. The fine powders thus produced were processed to produce spherical granules, using 600 g of purified sucrose that was obtained by shifting through 20–28 mesh as a core, while spraying a solution of 25 g of hydroxypropyl cellulose in 475 g of ethyl alcohol. The granules were then dried for 3 hours at 55° C. These dried granules were then passed through a 14 mesh followed by passage through a 28 mesh. The granules which did not go through the 28 mesh were taken as non-coated granules D. The formulation of this non-coated granules D was as follows:

| Component | % by weight |
|---|---|
| Diclofenac sodium | 38.3 |
| Fumaric acid | 19.2 |
| Corn starch | 8.2 |
| Purified sucrose | 32.9 |
| Hydroxypropyl cellulose | 1.4 |
| Total | 100.0 |

(2) Preparation of long-acting granules D-1 of this invention 600 g of non-coated granules D was placed into a coating apparatus with fluidized bed. The granules were spray coated with 900 g of a coating liquid having the following composition according to a conventional method to produce long-acting granules D-1. The amount of the coat was about 6% based on the weight of the non-coated granules.

| Component | % by weight |
|---|---|
| Aminoalkyl methacrylate copolymer | 3.3 |
| Polyethylene glycol | 0.5 |
| Talc | 0.2 |
| Ethyl alcohol | 96.0 |
| Total | 100.0 |

Example 6

(1) Preparation of non-coated granules E:

To mixed powders of 700 g of diclofenac sodium, 350 g of fumaric acid, 100 g of corn starch, 600 g of lactose, and 400 g of purified sucrose, was added a solution of 60 g of hydroxypropyl cellulose in 540 g of purified water, and the mixture was kneaded. The kneaded product was processed to produce spherical granules using a cylindrical granulator. The granules were then dried for 3 hours at 55° C. These dried granules were then passed through a 16 mesh followed by passage through a 30 mesh. The granules which did not go through the 30 mesh were taken as non-coated granules E. The formulation of this non-coated granules E was as follows:

| Component | % by weight |
|---|---|
| Diclofenac sodium | 31.8 |
| Fumaric acid | 15.8 |
| Corn starch | 4.5 |
| Lactose | 27.1 |
| Purified sucrose | 18.1 |
| Hydroxypropyl cellulose | 2.7 |

| Component | % by weight |
| --- | --- |
| Total | 100.0 |

(2) Preparation of long-acting granules E-1 of this invention 500 g of non-coated granules E was placed into a coating apparatus with fluidized bed. The granules were spray coated with 2,083 g of a coating liquid having the following composition according to a conventional method to produce long-acting granules E-1. The amount of the coat was about 30% based on the weight of the non-coated granules.

| Component | % by weight |
| --- | --- |
| Methacrylic acid copolymer L | 6.5 |
| Glycerine fatty acid ester | 0.5 |
| Talc | 0.2 |
| Ethyl alcohol | 92.8 |
| Total | 100.0 |

Comparative Example 1

(1) Preparation of non-coated granules F (non-coated granules not containing an organic acid):

800 g of diclofenac sodium and 400 g of corn starch were mixed and pulverized. The fine powders thus produced were processed to produce spherical granules, using 600 g of purified sucrose that was obtained by shifting through 20–28 mesh as a core, while spraying a solution of 25 g of hydroxypropyl cellulose in 475 g of ethyl alcohol. The granules were then dried for 3 hours at 55° C. These dried granules were then passed through a 14 mesh followed by passage through a 28 mesh. The granules which did not go through the 28 mesh were taken as non-coated granules F. The formulation of this non-coated granules F was as follows:

| Component | % by weight |
| --- | --- |
| Diclofenac sodium | 43.8 |
| Corn starch | 21.9 |
| Purified sucrose | 32.9 |
| Hydroxypropyl cellulose | 1.4 |
| Total | 100.0 |

(2) Preparation of coated granules F-1 not containing an organic acid 600 g of non-coated granules F was placed into a coating apparatus with fluidized bed. The granules were spray coated with 1,667 g of a coating liquid having the following composition according to a conventional method to produce coated granules F-1. The amount of the coat was about 20% based on the weight of the non-coated granules.

| Component | % by weight |
| --- | --- |
| Methacrylic acid copolymer S | 6.5 |
| Glycerine fatty acid ester | 0.5 |
| Talc | 0.2 |
| Ethyl alcohol | 92.8 |
| Total | 100.0 |

Comparative Example 2

Preparation of coated granules F-2 not containing an organic acid:

600 g of non-coated granules F was placed into a coating apparatus with fluidized bed. The granules were spray coated with 1,263 g of a coating liquid having the following composition according to a conventional method to produce coated granules F-2. The amount of the coat was about 8% based on the weight of the non-coated granules.

| Component | % by weight |
| --- | --- |
| Ethylcellulose | 2.7 |
| Polyvinyl pyrrolidone K-30 | 0.9 |
| Talc | 0.2 |
| Ethyl alcohol | 96.2 |
| Total | 100.0 |

Example 7

Preparation of long-acting tablets G-1 of this invention 375 g of diclofenac sodium, 100 g of fumaric acid, 500 g of dibasic calcium phosphate, 262.5 g of lactose, and 12.5 g of talc were homogeneously mixed and compress-molded to produce tablets, each tablet having a weight of 250 mg and a diameter of 9 mm. The formulation of the tablets was as follows:

| Component | % by weight |
| --- | --- |
| Diclofenac sodium | 30.0 |
| Fumaric acid | 8.0 |
| Dibasic calcium phosphate | 40.0 |
| Lactose | 21.0 |
| Talc | 1.0 |
| Total | 100.0 |

1000 g of the tablets were placed into a coating pan and were spray coated with a coating liquid having the following composition according to a conventional method until the weight increase per tablet reaches 10 mg. Long-acting tablets G-1 were thus produced.

| Component | % by weight |
| --- | --- |
| Ethylcellulose | 2.7 |
| Polyvinyl pyrrolidone K30 | 0.9 |
| Talc | 0.2 |
| Ethyl alcohol | 96.2 |
| Total | 100.0 |

Example 8

Preparation of long-acting capsules H-1 of this invention 14.37 g of long-acting granules C-1 prepared in Example 4 and 5.13 g of non-coated granules F prepared in Comparative Example 1 were homogeneously mixed and filled into capsules, 195 mg per capsule, to obtain long-acting capsules H-1.

Comparative Example 3

Preparation of long-acting capsules I-1 not containing an organic acid 14.37 g of coated granules F-1 prepared in Comparative Example 1 and 5.13 g of non-coated granules F prepared in Comparative Example 1 were homogeneously mixed and filled into capsules, 195 mg per capsules, to obtain long-acting capsules I-1.

Test Example 1

Figure 1:
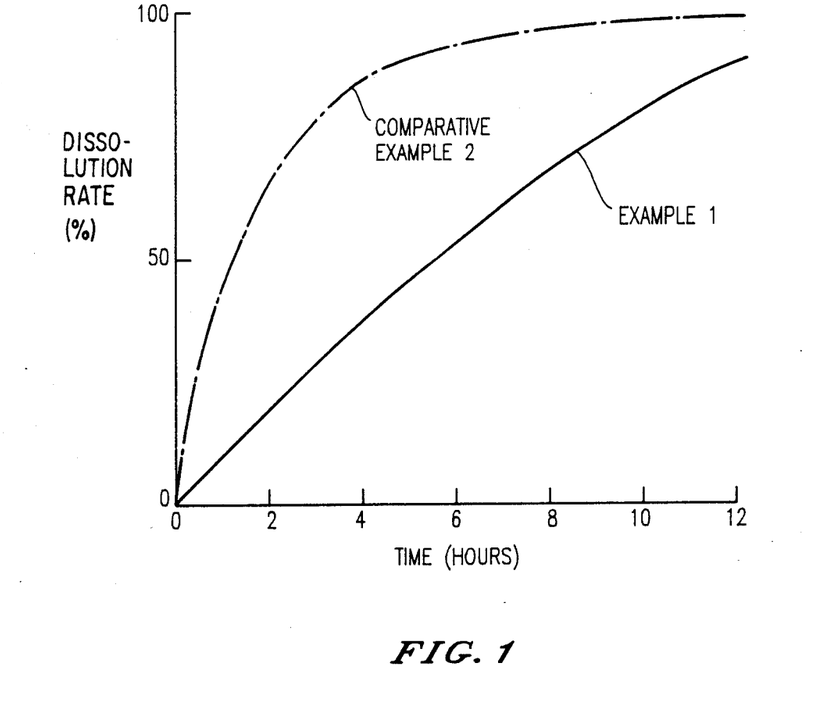
FIG. 1 is a drawing showing the results obtained in the dissolution test of Test Example 1 hereinafter, wherein the change in the dissolution rate of diclofenac sodium over time is depicted.

The diclofenac sodium dissolution from the long-acting granules prepared in Example 1 and the coated granules prepared in Comparative Example 2 were measured by the rotating paddle method (Japan Pharmacopeia, 11th Edition) using a buffer at pH 6.8. The results are shown in FIG. 1. Suppressed release of diclofenac sodium from the long-acting granules as compared with the coated granules not containing an organic acid was demonstrated.

Test Example 2

Figure 2:
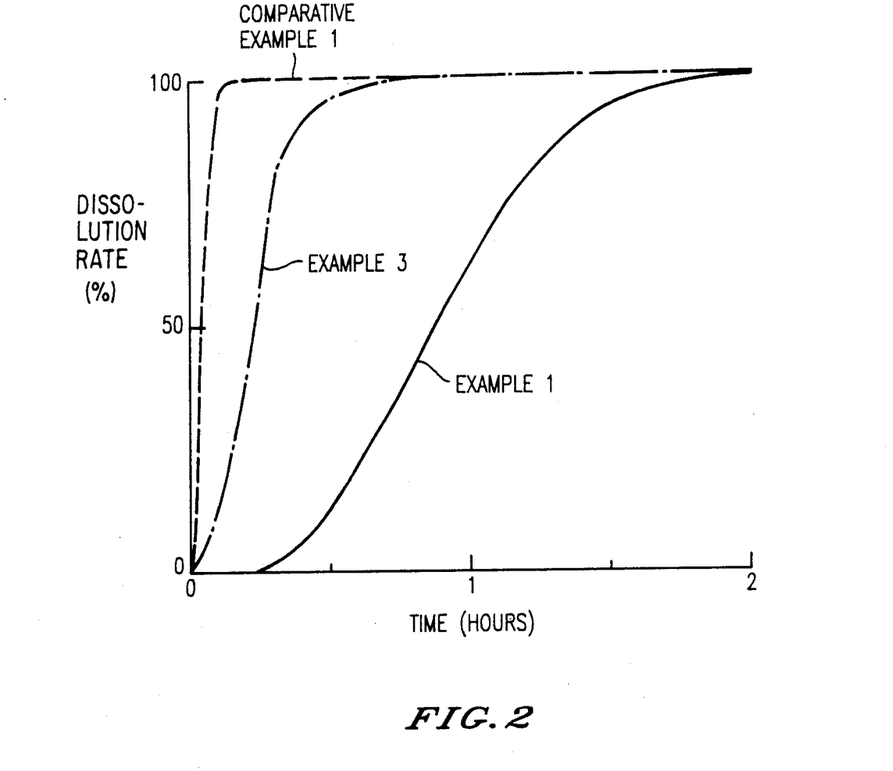
FIG. 2 is a drawing showing the results obtained in Test Example 2 hereinafter, wherein the change in the dissolution rate of dichlofenac sodium over time is depicted.

The diclofenac sodium dissolution from the long-acting granules prepared in Examples 3 and 4, and that of the coated granules, not containing an organic acid, prepared in Comparative Example 1, were measured by the rotating paddle method (Japan Pharmacopeia, 11th Edition) using a buffer at pH 7.5. The results are shown in FIG. 2. Suppressed release of diclofenac sodium from the long-acting granules as compared with the coated granules which do not contain an organic acid was demonstrated.

Test Example 3

Figure 3:
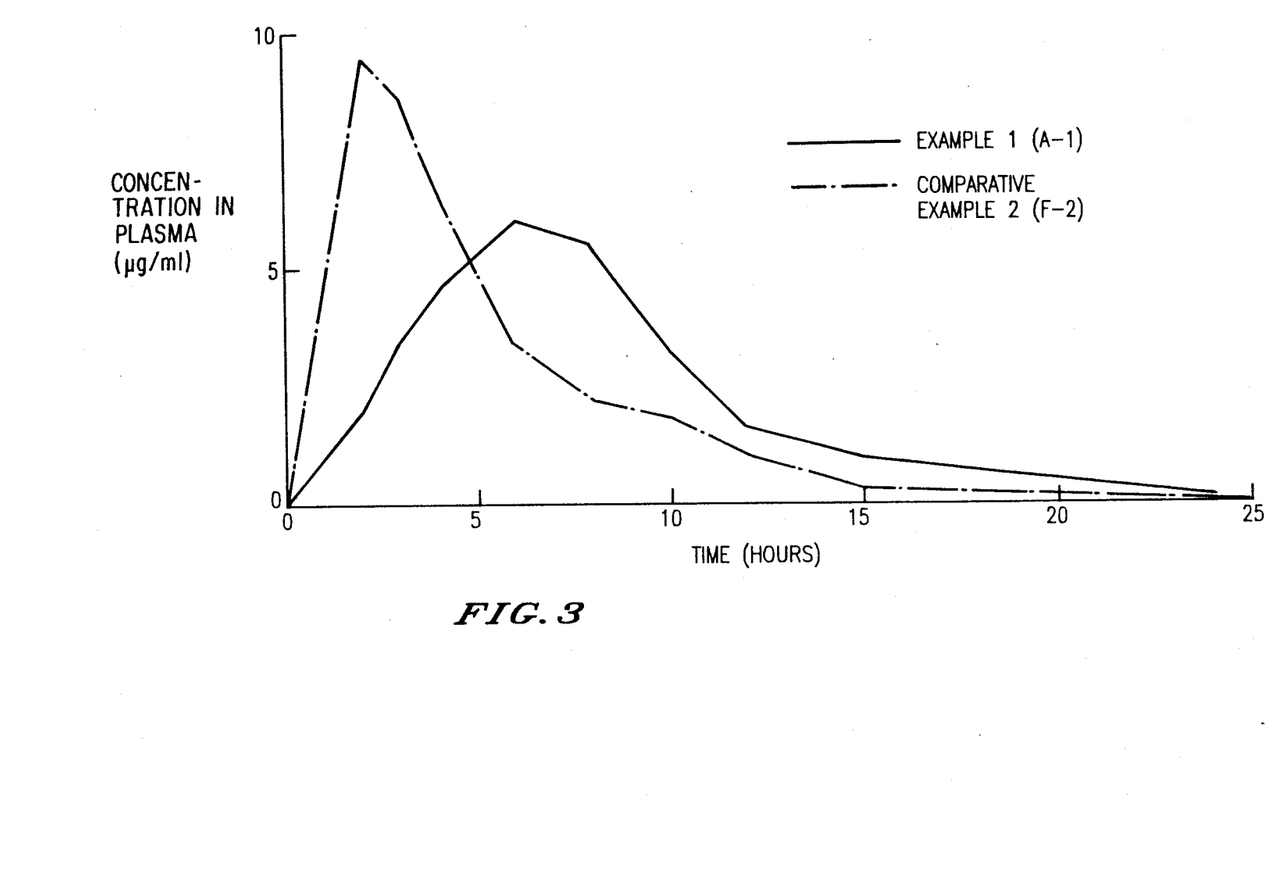
FIG. 3 is a drawing showing the results obtained in Test Example 3 hereinafter, wherein the change in plasma dichlofenac concentration over time is depicted.

123.2 mg of long-acting granules A-1 prepared in Example 1 and coated granules F-2, not containing an organic acid, prepared in Comparative Example 2, were administered to beagles which were fasted overnight to measure the diclofenac concentration in plasma at predetermined intervals by means of HPLC. The results are shown in FIG. 3. Prolonged plasma concentration of the long-acting granules A-1 as compared with the coated granules F-2, not containing an organic acid, was demonstrated.

Example 9

(1) Preparation of non-coated granules J:

525 g of diclofenac sodium, 130 g fumaric acid, 55 g of talc, and 10 g of corn starch were mixed and pulverized. The fine powders thus produced were processed to produce spherical granules, using 480 g of purified sucrose that was obtained by shifting through 24–28 mesh as a core, while spraying a solution of 27 g of hydroxypropyl cellulose in 513 g of ethyl alcohol. The granules were then dried for 3 hours at 55° C. These dried granules were then passed through a 14 mesh followed by passage through a 32 mesh. The granules which did not go through the 32 mesh were taken as non-coated granules J. The formulation of this non-coated granules J was as follows:

| Component | % by weight |
| --- | --- |
| Diclofenac sodium | 42.8 |
| Fumaric acid | 10.6 |
| Talc | 4.5 |
| Corn starch | 0.8 |
| Hydroxypropyl cellulose | 2.2 |
| Purified sucrose | 39.1 |
| Total | 100.0 |

(2) Preparation of long-acting granules J-1 of this invention:

500 g of non-coated granules J was placed into a coating apparatus with a fluidized bed. The granules were spray coated with 1,736 g of a coating liquid having the following composition according to a conventional method to produce long-acting granules J-1. The amount of the coat was about 25% of the weight of the non-coated granules.

| Component | % by weight |
| --- | --- |
| Methacrylic acid copolymer S | 6.5 |
| Glycerine fatty acid ester | 0.5 |
| Talc | 0.2 |
| Ethyl alcohol | 92.8 |
| Total | 100.0 |

(3) Preparation of non-coated granules K:

337.5 g of diclofenac sodium, 760.5 g of corn starch, and 222 g of purified sucrose were mixed and pulverized. The fine powders thus produced were processed to produce spherical granules, using 523.5 g of purified sucrose that was obtained by shifting through 24–28 mesh as a core, while spraying a solution of 25.5 g of hydroxypropyl cellulose in 484.5 g of ethyl alcohol. The granules were then dried for 3 hours at 55° C. These dried granules were then passed through a 14 mesh followed by passage through a 32 mesh. The granules which did not go through the 32 mesh were taken as non-coated granules K. The formulation of this non-coated granules K was as follows:

| Component | % by weight |
| --- | --- |
| Diclofenac sodium | 18.1 |
| Corn starch | 40.6 |
| Hydroxypropyl cellulose | 1.4 |
| Purified sucrose | 39.9 |
| Total | 100.0 |

(4) Preparation of long-acting capsules L-1 of this invention 306.8 g of long-acting granules J-1, 249.2 g of non-coated granules K, and 4 g of talc were homogeneously mixed and filled into capsules, 280 mg per capsule, to obtain long-acting capsules L-1.

Test Example 4

Figure 4:
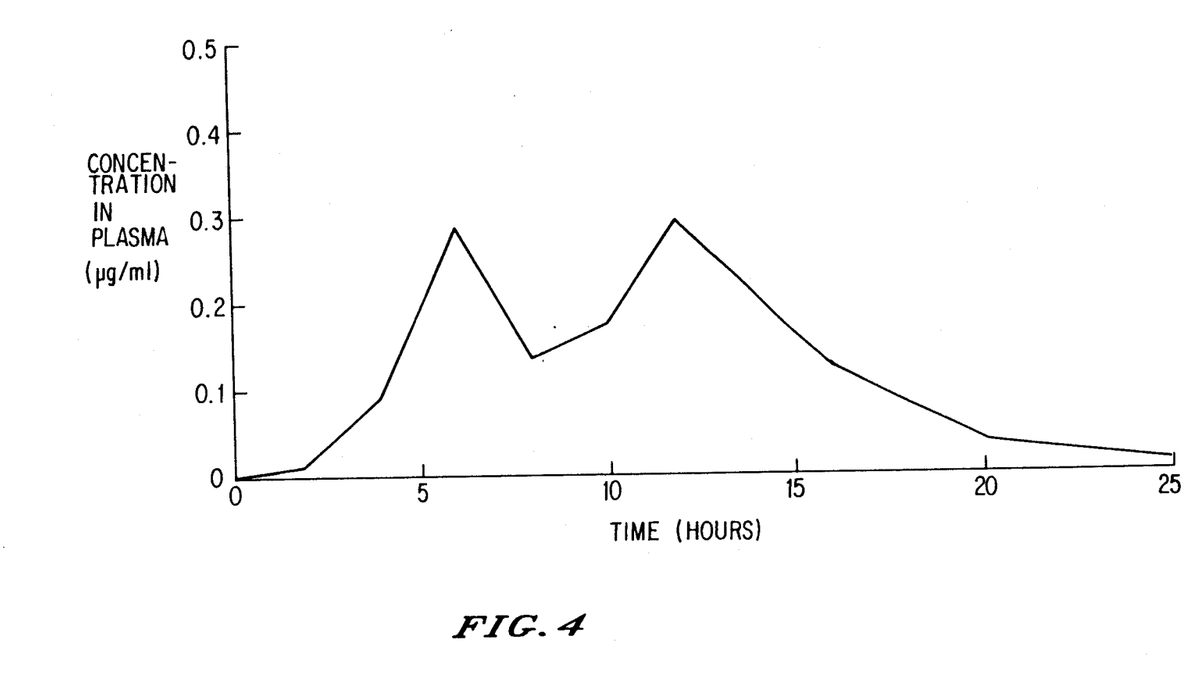
FIG. 4 is a drawing similar to FIG. 3 showing the results obtained in Test Example 4.

The long-acting granules L-1 prepared in Example 9 was administered to 3 healthy male adults at 30 minutes after meal together with 180 ml of water to measure the diclofenac concentration in plasma at predetermined intervals by means of HPLC. The results are shown in FIG. 4. A constant diclofenac concentration in plasma over a long period of time after the administration of the long-acting capsules was evidenced.

Example 10

(1) Preparation of non-coated granules M:

800 g of diclofenac sodium and 200 g of corn starch were mixed and pulverized to produce fine powders N. Separately, 200 g of fumaric acid and 200 g of corn starch were mixed and pulverized to produce fine powders 0. Fine powders N and then fine powders 0 were fed to a granulator, using 600 g of purified sucrose that was obtained by shifting through 24–28 mesh as a core, while spraying a shifting solution of 30 g of hydroxypropyl cellulose in 570 g of ethyl alcohol. The granules were then dried for 3 hours at 55° C. These dried granules were then passed through a 14 mesh followed by passage through a 28 mesh. The granules which did not go through the 28 mesh were taken as non-coated granules M. The formulation of this non-coated granules M was as follows:

| Component | % by weight |
| --- | --- |
| Diclofenac sodium | 39.4 |
| Fumaric acid | 9.9 |
| Corn starch | 19.7 |
| Purified sucrose | 29.5 |
| Hydroxypropyl cellulose | 1.5 |
| Total | 100.0 |

(2) Preparation of long-acting granules M-1 of this invention:

600 g of non-coated granules M was placed into a coating apparatus with a fluidized bed. The granules were spray coated with 1,667 g of a coating liquid having the following composition according to a conventional method to produce long-acting granules M-1. The amount of the coat was about 20% of the weight of the non-coated granules.

| Component | % by weight |
| --- | --- |
| Methacrylic acid copolymer L | 6.5 |
| Glycerine fatty acid ester | 0.5 |
| Talc | 0.2 |
| Ethyl alcohol | 92.8 |
| Total | 100.0 |

Obviously, numerous modifications and variations of the present invention are possible in light of the above teachings. It is therefore to be understood that the scope of the appended claims, the invention may be practiced otherwise than as specifically described herein.

What is claimed is:

1. A long-acting diclofenac sodium preparation comprising a sustained-release diclofenac sodium component which is prepared by coating a sustained-release coat onto a pharmaceutical composition comprising 100 parts by weight of diclofenac sodium and 2-50 parts by weight of an organic acid.

2. A long-acting diclofenac sodium preparation comprising: (i) a sustained-release diclofenac sodium component and (ii) a rapid-release diclofenac sodium component in an amount of 10-50% by weight as diclofenac sodium against the total amount of diclofenac sodium in the preparation.

3. A long-acting diclofenac sodium preparation according to claim 1, wherein said sustained-release coat comprises an intestinally soluble polymer which is soluble in water at an acidity level in the range of about pH 5.5-7.

4. A long-acting diclofenac sodium preparation according to claim 3, wherein said sustained-release coat comprises an intestinally soluble polymer which is soluble in water at an acidity level of about pH 7.

5. A long-acting diclofenac sodium preparation according to claim 1, wherein said sustained-release coat comprises a water insoluble polymer.

6. A long-acting diclofenac sodium preparation according to claim 1, wherein said sustained-release coat comprises 1 part by weight of ethylcellulose, 0.2-0.5 part by weight of polyvinyl pyrrolidone, and 0.01-1.5 parts by weight of talc.

7. A long-acting diclofenac sodium preparation according to claim 1, wherein the amount of said sustained-release coat on the pharmaceutical composition is 1-80% by weight of said pharmaceutical composition.

8. A long-acting diclofenac sodium preparation according to claim 1, wherein the amount of said sustained-release coat on the pharmaceutical composition is 1-80% by weight of said pharmaceutical composition.

9. A long-acting diclofenac sodium preparation according to claim 3, wherein the amount of said sustained-release coat on the pharmaceutical composition is 1-80% by weight of said pharmaceutical composition.

10. A long-acting diclofenac sodium preparation according to claim 4, wherein the amount of said sustained-release coat on the pharmaceutical composition is 1-80% by weight of said pharmaceutical composition.

11. A long-acting diclofenac sodium preparation according to claim 5, wherein the amount of said sustained-release coat on the pharmaceutical composition is 1-80% by weight of said pharmaceutical composition.

12. A long-acting diclofenac sodium preparation according to claim 6, wherein the amount of said sustained-release coat on the pharmaceutical composition is 1-80% by weight of said pharmaceutical composition.

13. A long-acting diclofenac sodium preparation according to claim 2, wherein the sustained-release diclofenac sodium component and the rapid-release diclofenac sodium component are mixed.

14. A long-acting diclofenac sodium preparation according to claim 2, wherein the sustained-release diclofenac sodium component and the rapid-release diclofenac sodium component form separate layers.

* * * * *